United States Patent
Kao

(10) Patent No.: US 11,530,840 B2
(45) Date of Patent: Dec. 20, 2022

(54) FILTRATION DEVICE

(71) Applicant: JOIN POWER COMPANY, Taipei (TW)

(72) Inventor: Wen-Ling Kao, Taipei (TW)

(73) Assignee: JOIN POWER COMPANY, Taipei (TW)

( * ) Notice: Subject to any disclaimer, the term of this patent is extended or adjusted under 35 U.S.C. 154(b) by 326 days.

(21) Appl. No.: 16/939,565

(22) Filed: Jul. 27, 2020

(65) Prior Publication Data

US 2022/0026106 A1    Jan. 27, 2022

(51) Int. Cl.
| | | |
|---|---|---|
| B01D 46/10 | (2006.01) |
| F24F 13/06 | (2006.01) |
| F24F 13/28 | (2006.01) |
| F24F 8/167 | (2021.01) |
| A61L 9/20 | (2006.01) |
| B01D 46/00 | (2022.01) |
| F24F 8/108 | (2021.01) |

(52) U.S. Cl.
CPC .............. *F24F 13/28* (2013.01); *A61L 9/205* (2013.01); *F24F 13/06* (2013.01); *B01D 46/0005* (2013.01); *B01D 46/0015* (2013.01); *F24F 8/108* (2021.01); *F24F 8/167* (2021.01)

(58) Field of Classification Search
CPC ............ B01D 46/0005; B01D 46/0006; B01D 46/0028; B01D 46/026; B01D 46/0049; B01D 46/10; A61L 9/205; A61L 2209/14; F24F 13/28; F24F 13/06; F24F 8/167
USPC ......... 55/467, 497, 385.2, 472; 96/384, 421, 96/372; 422/186.06
See application file for complete search history.

(56) References Cited

U.S. PATENT DOCUMENTS

| | | | | | |
|---|---|---|---|---|---|
| 4,846,859 | A | * | 7/1989 | Nobiraki | F24F 13/28 96/384 |
| 5,443,625 | A | * | 8/1995 | Schaffhausen | F21V 33/0096 55/472 |
| 7,056,372 | B2 | * | 6/2006 | Cheng | B01D 46/521 96/372 |
| 7,323,146 | B2 | * | 1/2008 | Kim | B01D 46/10 422/186.06 |
| 2001/0049927 | A1 | * | 12/2001 | Toepel | B01D 46/88 55/385.2 |
| 2010/0150787 | A1 | * | 6/2010 | Choi | B01D 46/0028 55/385.6 |
| 2011/0297000 | A1 | * | 12/2011 | Kotani | G03B 21/16 96/421 |

(Continued)

*Primary Examiner* — Minh Chau T Pham
(74) *Attorney, Agent, or Firm* — Muncy, Geissler, Olds & Lowe, P.C.

(57) ABSTRACT

A filtration device is provided, configured to be assembled between a tube seat and an air diffuser of a ventilation system, including: a main body, at least one filter and at least one light source. The main body includes an air inlet connected with the tube seat, an air outlet connected with the air diffuser and a shielding portion blocking between the air inlet and the air outlet. The shielding portion defines at least one passage. The at least one filter is disposed on the main body and corresponds to the at least one passage. The at least one filter has a photocatalyst material disposed thereon. An illumination area of the at least one light source corresponds to the at least one passage. A distance between the at least one light source and the at least one filter is smaller than or equal to 100 mm.

10 Claims, 7 Drawing Sheets

(56) References Cited

U.S. PATENT DOCUMENTS

| | | | |
|---|---|---|---|
| 2011/0314781 A1* | 12/2011 | Greist | B01D 46/42 55/497 |
| 2013/0081224 A1* | 4/2013 | Van Der Kool | B01D 46/10 15/349 |
| 2014/0338528 A1* | 11/2014 | Hauville | B08B 15/00 55/467 |

* cited by examiner

FILTRATION DEVICE

BACKGROUND OF THE INVENTION

Field of the Invention

The present invention relates to a filtration device.

Description of the Prior Art

Generally, an interior space is equipped with a ventilation system to maintain air circulation and improve air quality. In operation, the ventilation system discharges the air into the interior space through a vent and withdraws a predetermined volume of the air from the interior space. Most of the air withdrawn from the interior space is processed in the ventilation system, and the rest is discharged to an external environment. Since the ventilation system has limited filtration effect, a filtration device is assembled to the vent so as to further purify the air discharged therethrough.

However, a conventional filtration device usually includes several filter layers, which results in disadvantages of low air output and poor ventilation. Moreover, the conventional filtration device or part of its components is directly assembled to a tube seat or an air diffuser of the vent so that the whole vent has to be replaced for assembling the filtration device, which is inconvenient to be assembled and repaired. In addition, the conventional filtration device cannot ensure that the air discharged from the vent actually passed through an effective filtration area of the filtration device, which results in poor filtration effect.

The present invention is, therefore, arisen to obviate or at least mitigate the above-mentioned disadvantages.

SUMMARY OF THE INVENTION

The main object of the present invention is to provide a filtration device which provides good filtration effect and a wide application range.

To achieve the above and other objects, the present invention provides a filtration device configured to be assembled between a tube seat and an air diffuser of a ventilation system, the filtration device including: a main body, at least one filter and at least one light source. The main body includes an air inlet configured to be connected with the tube seat, an air outlet configured to be connected with the air diffuser and a shielding portion blocking between the air inlet and the air outlet. The shielding portion defines at least one passage. The at least one filter is disposed on the main body and corresponds to the at least one passage. The at least one filter has at least one photocatalyst material disposed thereon. The at least one light source is disposed on the main body. An illumination area of the at least one light source corresponds to the at least one passage, and a distance between the at least one light source and the at least one filter is smaller than or equal to 100 mm.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
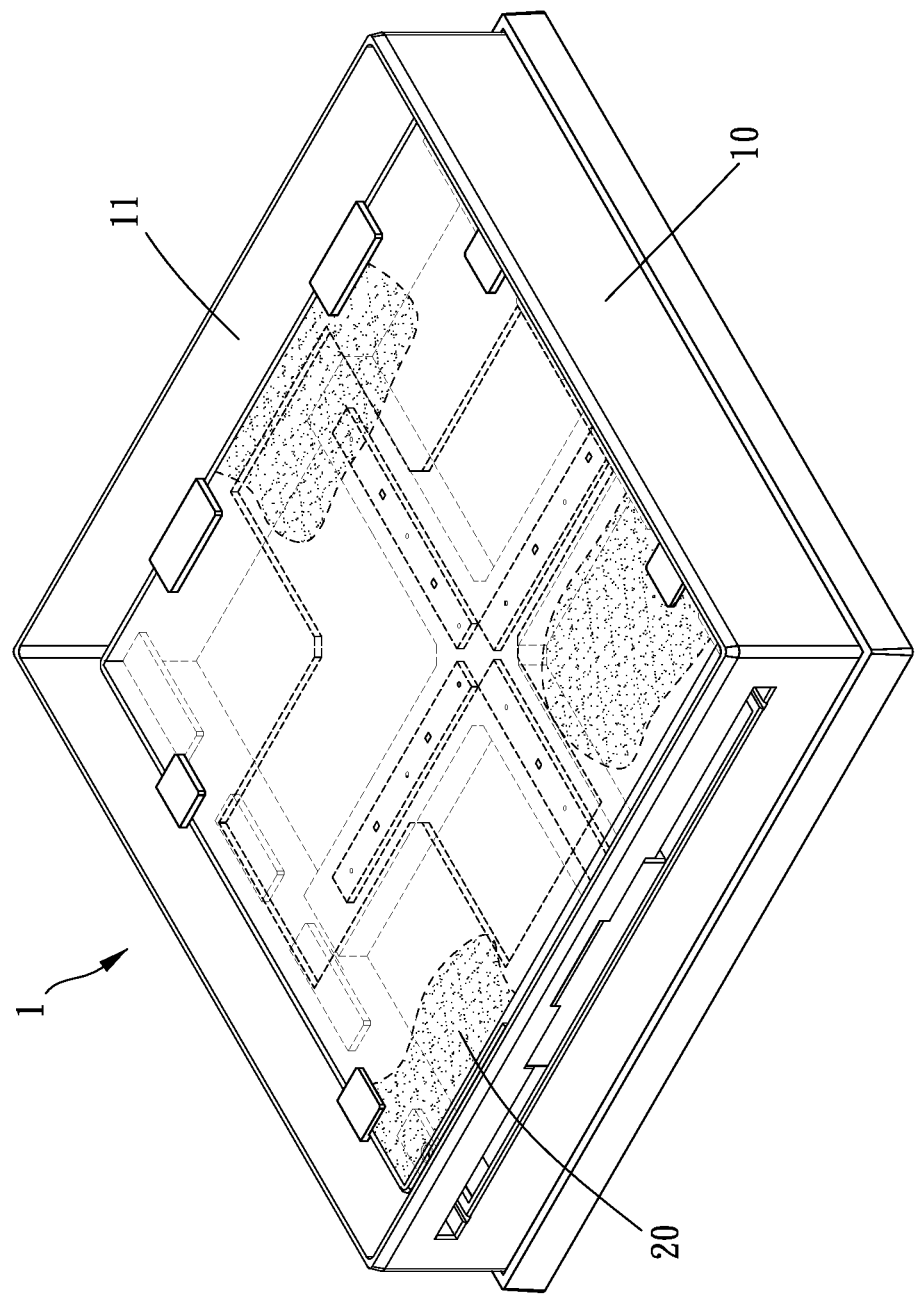
FIG. 1 is a stereogram of a preferable embodiment of the present invention.

Please refer to FIGS. 1 to 6 for a preferable embodiment of the present invention. A filtration device 1 of the present invention is configured to be assembled between a tube seat 100 and an air diffuser 200 of a ventilation system. The filtration device 1 includes a main body 10, at least one filter 20 and at least one light source 30.

The main body 10 includes an air inlet 11 configured to be connected with the tube seat 100, an air outlet 12 configured to be connected with the air diffuser 200 and a shielding portion 13 blocking between the air inlet 11 and the air outlet 12. The shielding portion 13 defines at least one passage 131. The at least one filter 20 is disposed on the main body 10 and corresponds to the at least one passage 131. The at least one filter 20 has at least one photocatalyst material disposed thereon. The at least one light source 30 is disposed on the main body 10. An illumination area of the at least one light source 30 corresponds to the at least one passage 131, and a distance between the at least one light source 30 and the at least one filter 20 is smaller than or equal to 100 mm. Therefore, the at least one passage 131 allows air to pass through an effective filtration area of the at least one filter 20; the at least one light source 30 has a broad illumination area which preferably corresponds to part of the at least one filter 20 corresponding to the at least one passage 131, and light emitted from the at least one light source 30 is directly projected to the at least one filter 20 in a height direction H of the main body 10, which provides sufficient light intensity to effectively activate the at least one photocatalyst material to produce bactericidal effect. The filtration device 1 has good bactericidal and filtration effects and a wide application range.

In the height direction H, the at least one filter 20 and the at least one light source 30 are located at two opposite sides of the at least one passage 131, and the light emitted from the at least one light source 30 is projected to the at least one filter 20 through the passage 131. The at least one filter 20 preferably further has a nano-silver material disposed thereon so as to increase anti-bacteria effect. In this embodiment, each of the at least one light source 30 is a visible light-emitting diode which has a small volume and provides sufficient light intensity and a wide application range, and the at least one photocatalyst material is activated by visible light to generate free radicals so as to have bactericidal effect. However, the at least one photocatalyst material may be selected from materials activated by ultraviolet light, and ultraviolet light is used as the at least one light source.

Specifically, the main body 10 further includes at least one assembling frame 14 extending inwardly, and the at least one light source 30 is disposed on the at least one assembling frame 14. At least one of the at least one assembling frame 14 is connected between two sidewalls of the main body 10 so that part of the at least one filter 20 located in the middle of the main body 10 can receive light with sufficient intensity to have good bactericidal effect. The filtration device 1 further includes at least one circuit device 40 having at least one of the at least one light source 30 disposed thereon. The at least one circuit device 40 may be a light strip, printed circuit board or the like for easy assembling. Preferably, each of the at least one assembling frame 14 has a plurality of assembling convex portions 141 spaced apart from one another, and each of the at least one circuit device 40 has a plurality of assembling concave portions 41 which are correspondingly connected with the plurality of assembling convex portions 141 for easy assembling, replacement and maintenance. However, each of the at least one assembling frame may have the plurality of assembling concave portions, and each of the at least one circuit device may have the plurality of assembling convex portions; each of the at least one circuit device may be directly attached to or stuck on one of the at least one assembling frame.

Figure 2:
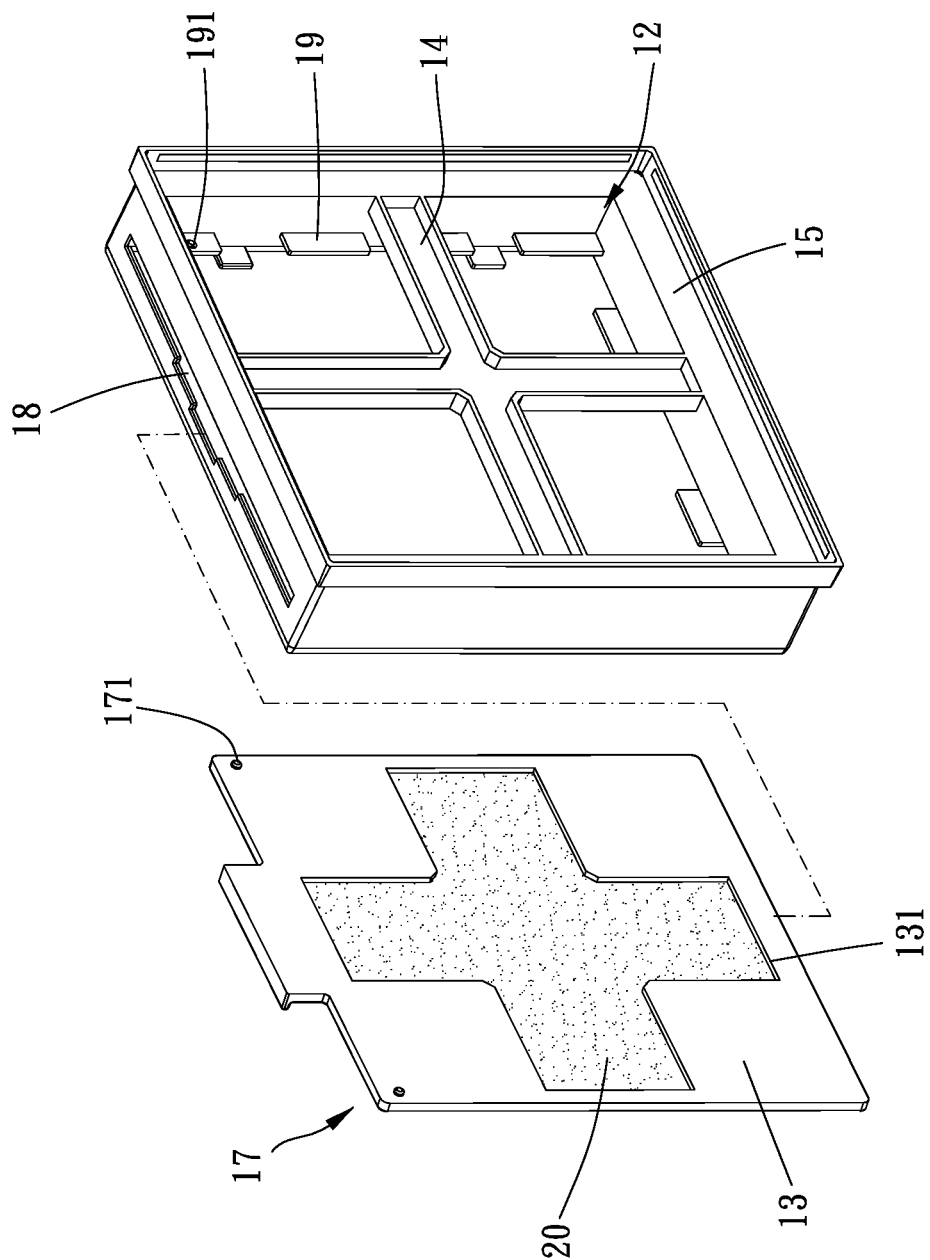
FIG. 2 is a partial breakdown drawing of a preferable embodiment of the present invention.
Figure 3:
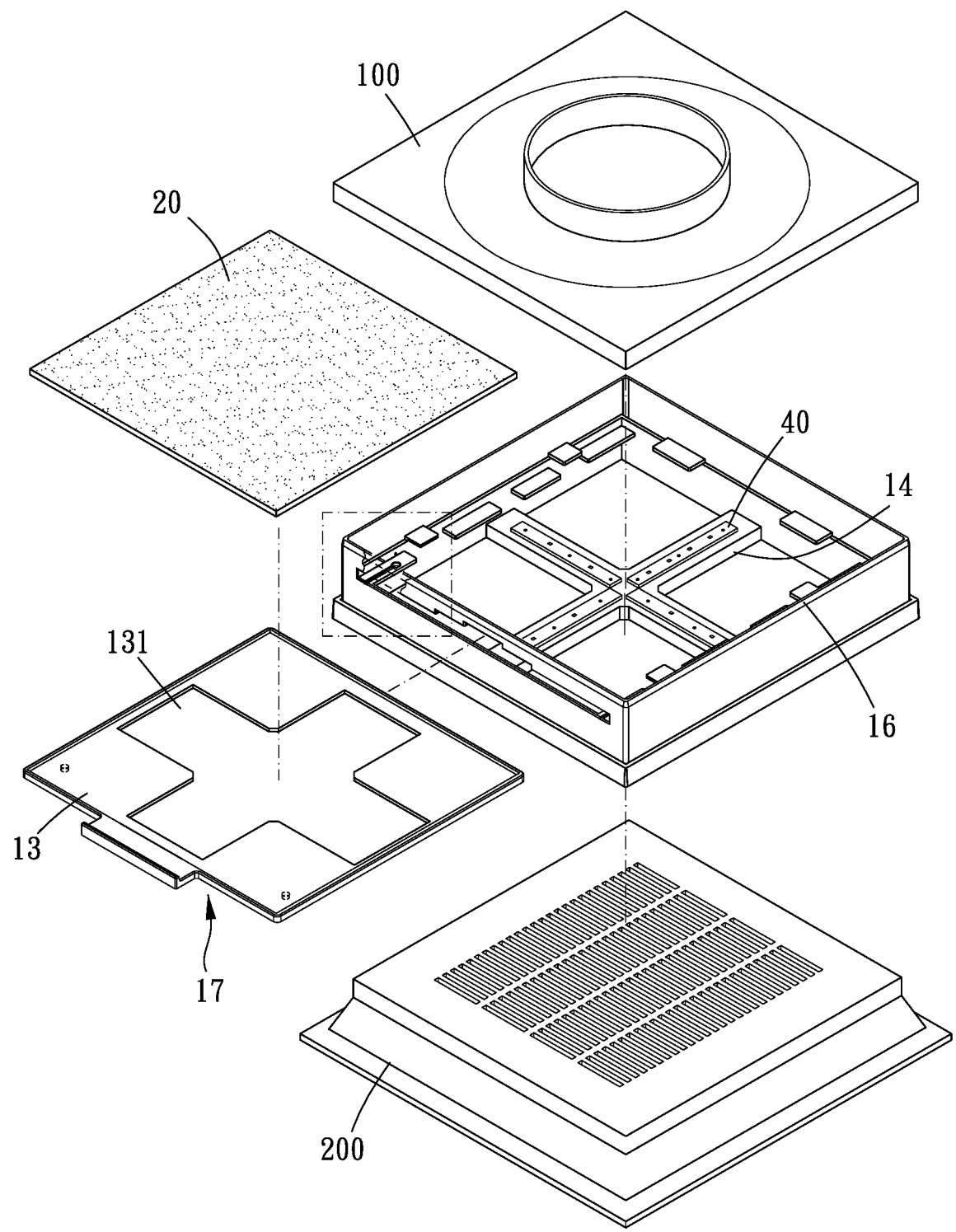
FIG. 3 is a breakdown drawing of a preferable embodiment of the present invention.
Figure 4:
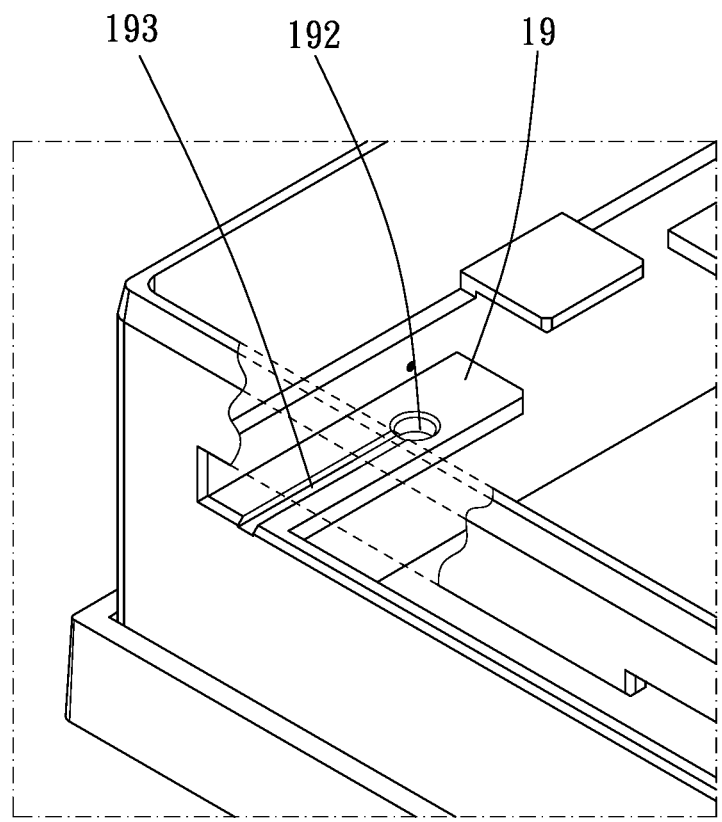
FIG. 4 is a partial enlargement of FIG. 3.
Figure 5:
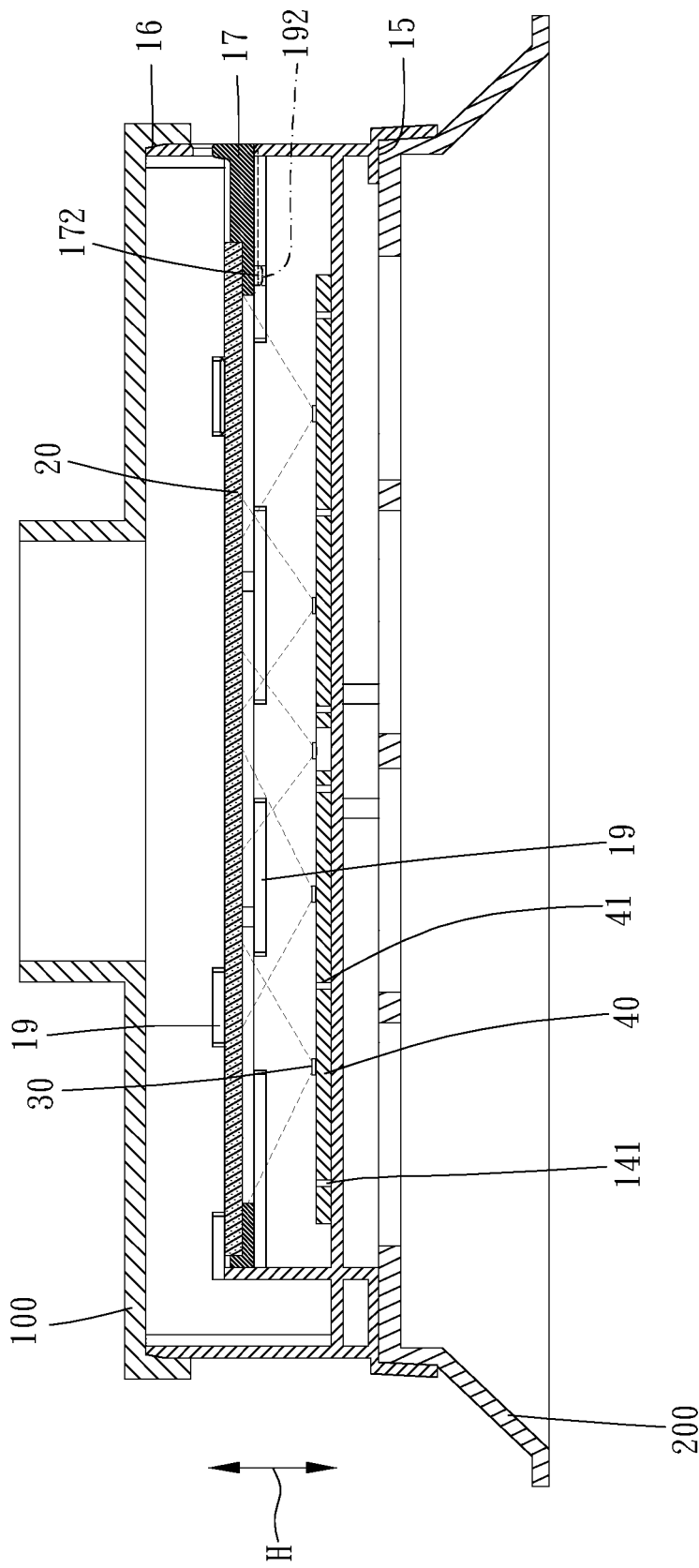
FIGS. 5 and 6 are schematic diagrams showing operation of a preferable embodiment of the present invention.
Figure 6:
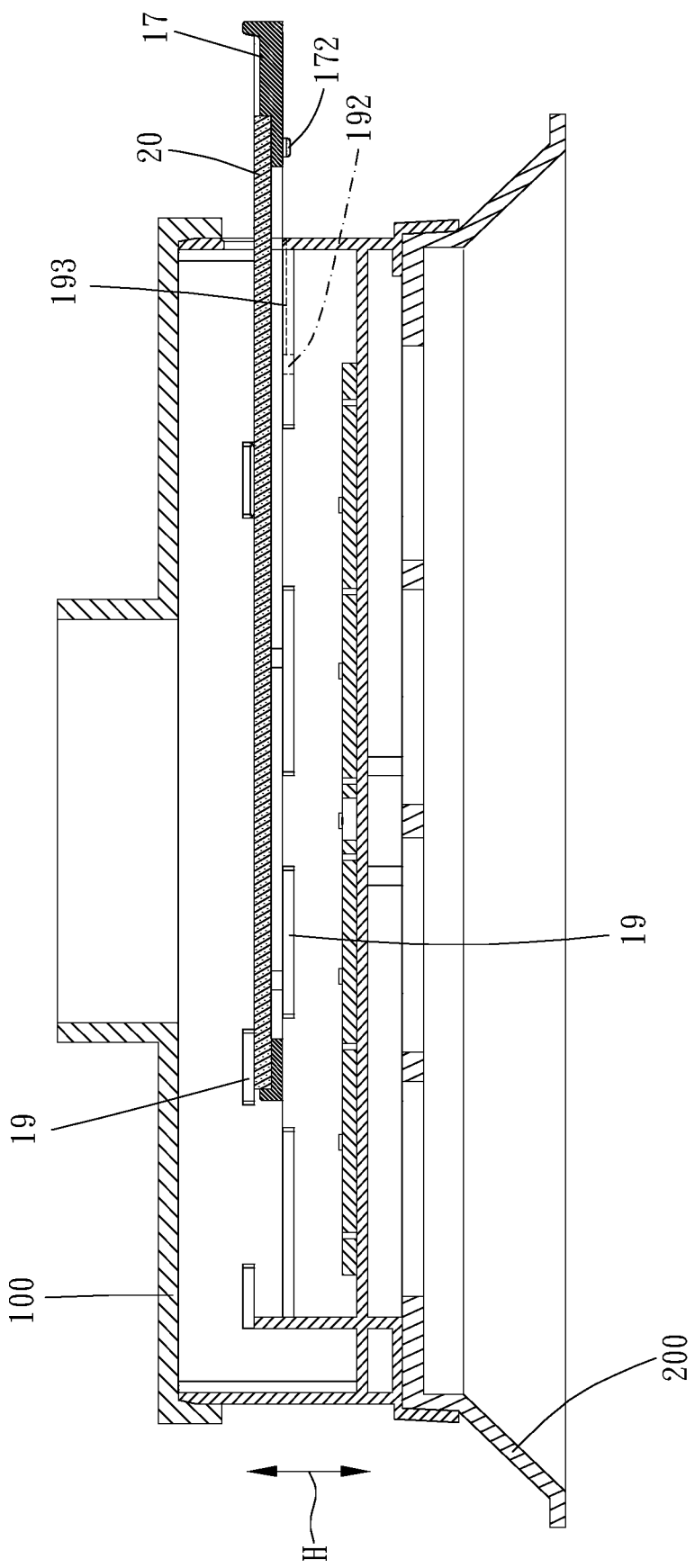

Please refer to FIGS. 1 to 3, in this embodiment, a shielding area of the shielding portion 13 is larger than or equal to one fifth of a cross sectional area of the air inlet 11, and the at least one passage 131 extends in a cross shape, which can effectively guide a direction of an airflow. The at least one assembling frame 14 is integrally connected between each sidewalls of the main body 10 and corresponds to the at least one passage 131 so as to have good structural strength. The at least one light source 30 is disposed on a side of the at least one assembling frame 14 facing the air inlet 11, and the at least one filter 20 is located at a side of the at least one passage 131 adjacent to the air inlet 11. The light emitted from the at least one light source 30 is projected in a direction toward the air inlet 11 so that the light is free of interference of external light and the at least one photocatalyst material can be effectively activated. However, the at least one passage may be configured as other configurations such as circular, rectangular, etc., according to one of various requirements; the at least one light source may be irradiated in different directions according to a position of each of the at least one filter.

An inner surface of the main body 10 has a stepped portion 15 circumferentially disposed thereon and adjacent to the air outlet 12, and the stepped portion 15 is configured to be abuttable against an outer peripheral surface of the air diffuser 200. An outer peripheral surface of the main body 10 has a guiding portion 16 disposed thereon and adjacent to the air inlet 11, and the guiding portion is configured to be abuttable against an inner surface of the tube seat 100. Therefore, the filtration device 1 is convenient to be connected between the air diffuser 200 and the tube seat 100 with general specifications and an existing structure of a vent is unnecessary to be changed, which has a simple structure and a wide application range.

The main body 10 further includes a tray 17 detachably disposed between the air inlet 11 and the air outlet 12, and the tray 17 has the shielding portion 13 and the at least one passage 131. A sidewall of the main body 10 has a slot 18 disposed therethrough, and the tray 17 is movably inserted within the slot 18. The at least one filter 20 is disposed on the tray 17 so that the at least one filter 20 is convenient to be replaced. In other embodiments, the at least one filter may be disposed within the at least one passage. Please refer to FIGS. 5 and 6, the inner surface of the main body 10 preferably has a plurality of projections 19, and the plurality of projections 19 restrict the tray 17 in the height direction H. The tray 17 and at least one of the plurality of projections 19 respectively have a first positioning portion 171 and a second positioning portion 191 which are connectable with each other. One of the first positioning portion 171 and the second positioning portion 191 includes at least one engaging projection 172, and the other of the first positioning portion 171 and the second positioning portion 191 includes at least one engaging recession 192 which is engageable with the at least one engaging projection 172 so as to have a simple structure and good assembling stability. In this embodiment, the first positioning portion 171 includes two said engaging projections 172, and the second positioning portion 191 includes two said engaging recessions 192 which are disposed on two of the plurality of projections 19; the two of the plurality of projections 19 having the two said engaging recessions 192 respectively have a guiding groove 193 in communication with one of the two said engaging recessions 192 so as to guide the two said engaging projections 172 to move to the two said engaging recessions 192 in a moving direction of the tray 17. Preferably, the plurality of projections 19 are arranged in a high-low configuration in the height direction H, and the tray 17 is disposed between the plurality of projections 19 so as to have good assembling stability.

Figure 7:
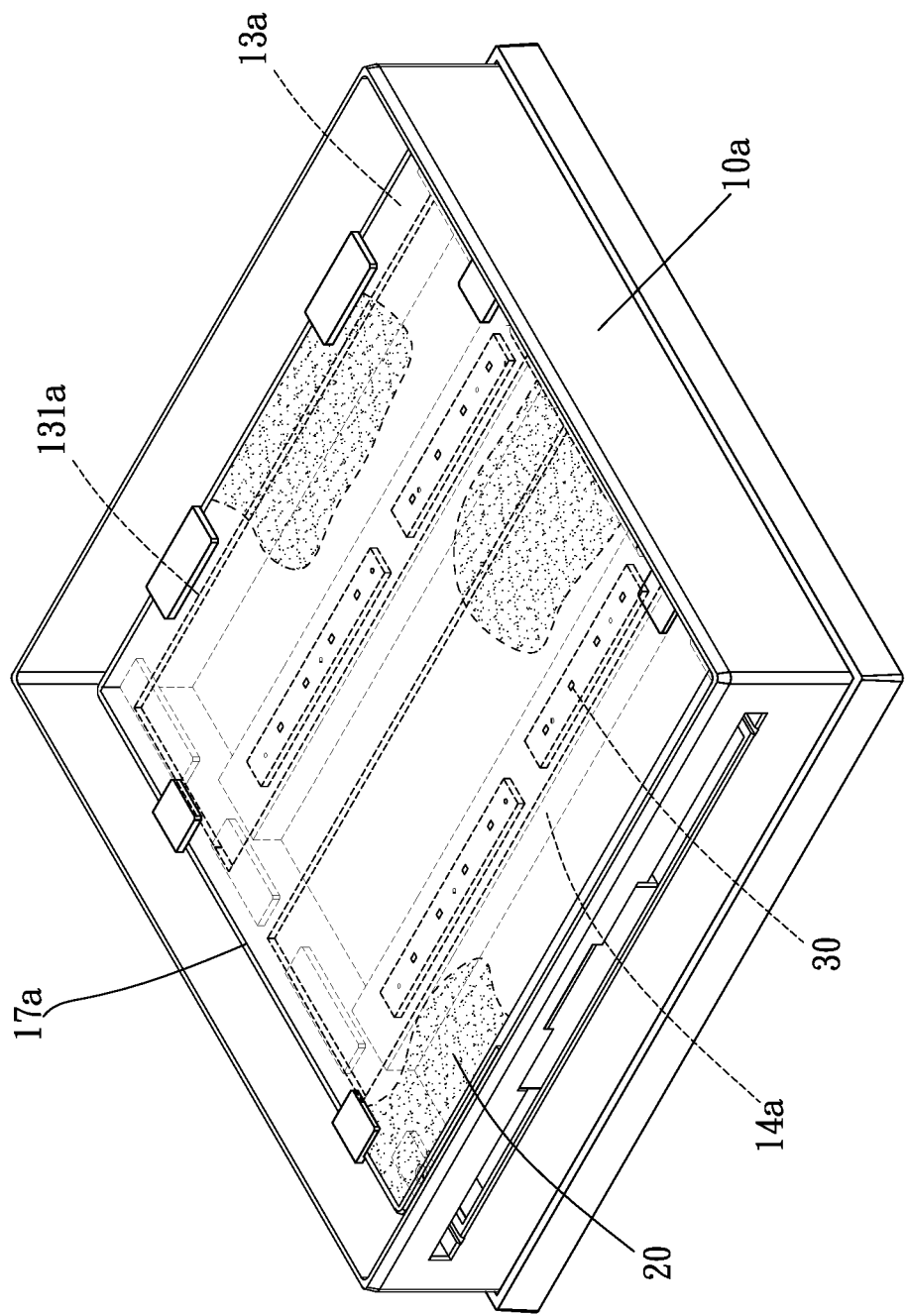
FIG. 7 is a stereogram of another preferable embodiment of the present invention.

Please refer to FIG. 7 showing another preferable embodiment of the present invention. The shielding portion 13a of the tray 17a defines two said passages 131a which are rectangular, and the main body 10a includes two said assembling frames 14a connected between two opposite sidewalls of the main body 10a. The two said assembling frames 14a correspond to the two said passages 131a so that the light emitted from the at least one light source 30 can be projected to part of the at least one filter 20 corresponding to the two said passages 131a through the two said passages 131a, which provides good bactericidal and filtration effects.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A filtration device, configured to be assembled between a tube seat and an air diffuser of a ventilation system, including:
    a main body, including an air inlet configured to be connected with the tube seat, an air outlet configured to be connected with the air diffuser and a shielding portion blocking between the air inlet and the air outlet, the shielding portion defining at least one passage;
    at least one filter, disposed on the main body and corresponding to the at least one passage, having at least one photocatalyst material disposed thereon; and
    at least one light source, disposed on the main body, an illumination area of the at least one light source corresponding to the at least one passage, a distance between the at least one light source and the at least one filter being smaller than or equal to 100 mm.

2. The filtration device of claim 1, wherein in a height direction of the main body, the at least one filter and the at least one light source are located at two opposite sides of the at least one passage.

3. The filtration device of claim 1, wherein the main body further includes at least one assembling frame extending inwardly, and the at least one light source is disposed on the at least one assembling frame.

4. The filtration device of claim 3, wherein at least one of the at least one assembling frame is connected between two sidewalls of the main body.

5. The filtration device of claim 1, wherein an inner surface of the main body has a stepped portion circumferentially disposed thereon and adjacent to the air outlet, and the stepped portion is configured to be abuttable against an outer peripheral surface of the air diffuser.

6. The filtration device of claim 1, wherein the main body further includes a tray detachably disposed between the air inlet and the air outlet, and the tray has the shielding portion and the at least one passage.

7. The filtration device of claim 6, wherein a sidewall of the main body has a slot disposed therethrough, and the tray is movably inserted within the slot.

8. The filtration device of claim 6, wherein an inner surface of the main body has a plurality of projections, the plurality of projections restrict the tray in a height direction of the main body, and the tray and at least one of the plurality of projections respectively have a first positioning portion and a second positioning portion which are connectable with each other.

9. The filtration device of claim 8, wherein in the height direction, the at least one filter and the at least one light source are located at two opposite sides of the at least one passage; the main body further includes at least one assembling frame extending inwardly, and the at least one light source is disposed on a side of the at least one assembling frame facing the air inlet; at least one of the at least one assembling frame is connected between two sidewalls of the main body; the filtration device further includes at least one circuit device having at least one of the at least one light source disposed thereon; each of the at least one light source is a visible light-emitting diode; each of the at least one assembling frame has a plurality of assembling convex portions spaced apart from one another, each of the at least one circuit device has a plurality of assembling concave portions which are correspondingly connected with the plurality of assembling convex portions; an inner surface of the main body has a stepped portion circumferentially disposed thereon and adjacent to the air outlet, and the stepped portion is configured to be abuttable against an outer peripheral surface of the air diffuser; an outer peripheral surface of the main body has a guiding portion disposed thereon and adjacent to the air inlet, and the guiding portion is configured to be abuttable against an inner surface of the tube seat; a sidewall of the main body has a slot disposed therethrough, and the tray is movably inserted within the slot; the at least one filter further has a nano-silver material disposed thereon; a shielding area of the shielding portion is larger than or equal to one fifth of a cross sectional area of the air inlet; the plurality of projections are arranged in a high-low configuration in the height direction, and the tray is disposed between the plurality of projections; one of the first positioning portion and the second positioning portion includes at least one engaging projection, and the other of the first positioning portion and the second positioning portion includes at least one engaging recession which is engageable with the at least one engaging projection.

10. The filtration device of claim 1, wherein light emitted from the at least one light source is projected in a direction toward the air inlet.

\* \* \* \* \*